United States Patent [19]

Kitney et al.

[11] Patent Number: 5,257,629
[45] Date of Patent: Nov. 2, 1993

[54] METHODS AND APPARATUS FOR THE EXAMINATION AND TREATMENT OF INTERNAL ORGANS

[75] Inventors: Richard I. Kitney, Fulham; Keith Straughan, Berkhamsted; Martin T. Rothman, London, all of United Kingdom

[73] Assignee: Intravascular Research Limited, Hertfordshire, United Kingdom

[21] Appl. No.: 777,253

[22] PCT Filed: May 29, 1990

[86] PCT No.: PCT/GB90/00830

§ 371 Date: Jan. 27, 1992

§ 102(e) Date: Jan. 27, 1992

[87] PCT Pub. No.: WO90/14601

PCT Pub. Date: Nov. 29, 1990

[30] Foreign Application Priority Data

May 26, 1989 [GB] United Kingdom ............... 8912198

[51] Int. Cl.$^5$ .............................................. A61B 8/12
[52] U.S. Cl. ............................. 128/662.06; 128/661.01
[58] Field of Search ............... 128/660.01, 660.06, 128/660.07, 662.06; 73/625, 626; 364/413.25

[56] References Cited

U.S. PATENT DOCUMENTS

| 4,398,540 | 8/1983 | Takemura et al. | 128/661.01 |
| 4,672,963 | 6/1987 | Barken | 128/303.1 |
| 4,821,731 | 4/1989 | Martinelli et al. | 128/662.06 |
| 4,893,629 | 1/1990 | Lewis | 128/660.07 |
| 4,917,097 | 4/1990 | Proudian et al. | 128/662.06 |
| 5,029,587 | 7/1991 | Boba et al. | 128/660.07 |
| 5,081,993 | 1/1992 | Kitney et al. | 128/661.08 |
| 5,125,409 | 6/1992 | Kajino et al. | 128/660.07 |

FOREIGN PATENT DOCUMENTS

WO89/04142 5/1989 PCT Int'l Appl. .

OTHER PUBLICATIONS

Gatzke et al., Hewlett-Packard Journal, vol. 34, No. 12, Dec. 1983, pp. 13-20 for Electronic Scanner for a Phased-Array Ultrasound Transducer.

*Primary Examiner*—Francis Jaworski
*Attorney, Agent, or Firm*—Tarolli, Sundheim & Covell

[57] ABSTRACT

The internal examination of a human organ is made by means of an ultrasonic probe inserted into the organ, and in one embodiment analogue echo signals from the probe are directly converted into digital signals before any signal processing is carried out. These signals are then stored in a digital computer where they are manipulated to produce a two-dimensional real-time representation of the interior of the organ for display on a terminal or as hard copy. The two-dimensional real-time image may be displayed simultaneously with a three-dimensional nonreal-time image produced by the system.

11 Claims, 4 Drawing Sheets

METHODS AND APPARATUS FOR THE EXAMINATION AND TREATMENT OF INTERNAL ORGANS

The present invention relates to methods and apparatus for the examination and treatment of the internal organs of the human body and is in some respects a variation on the method and apparatus disclosed in our U.S. Pat. No. 5,081,993.

In that earlier U.S. patent there is disclosed a method and apparatus for providing a three-dimensional non-real time image of an internal organ, such an artery, of the human body. This is achieved by means of ultrasonic signals transmitted from within the organ, the reflected signals being digitised and manipulated to give a wide variety of different three-dimensional views of the organ.

In contrast with the method and apparatus disclosed in our aforesaid earlier patent the prior art generally utilises analogue ultrasonic signals throughout which are then used to produce a real-time two-dimensional continuous image of the interior of the organ. Although this prior art has the advantage of immediacy it has the disadvantage of providing a relatively poor resolution image.

The invention of the present application is concerned with providing some of the advantages of the aforementioned analogue prior art systems combined with some of the advantages of the system disclosed in our above-mentioned earlier patent application.

According to the present invention, a system for providing an image of the interior of a human organ comprises a combination of the following features:
(a) a catheter for insertion into the human body;
(b) an ultrasonic transducer assembly mounted on the catheter;
(c) means for energising the transducer to generate ultrasonic signals;
(d) means for receiving the resultant analogue ultrasonic echo signals and converting them into digital signals before carrying out any processing of the echo signals:
(e) a digital computer to which the digital signals are fed;
(f) means for manipulating the digital signals in the digital computer to enable a two-dimensional real-time representation of the organ to be created; and
(g) means connected to the computer for visually displaying the two-dimensional representation.

According to a second aspect of the present invention the system for providing a two-dimensional real-time image is combined with the system of our U.S. Pat. No. 5,081,993 for providing a three-dimensional non-real-time image. This is preferably achieved by the use of a workstation which has means for displaying on the same screen both the two-dimensional real-time image and the three-dimensional non-real-time image.

According to a further aspect of the present invention the means for generating the two-dimensional real-time image includes at least two digital processing units adapted to operate in parallel.

According to yet another aspect of the present invention the ultrasonic transducer comprises a plurality of transducer elements connected in the system in such a way that the echo signal resulting from energisation of a first transducer element is received by a second transducer element. This differs from previous proposals in which the echo of the signal emitted by a given transducer element is also received by that same transducer element. With this proposed arrangement it is possible to significantly improve the azimuthal resolution of the ultrasonic signal.

According to yet another aspect of the present invention the echo signals resulting from energisation of the transducer elements are subject to signal processing in order to enhance the quality of the two dimensional image.

How the invention may be carried out may now be described by way of example only, and with reference to the accompanying drawings in which.

Figure 1:
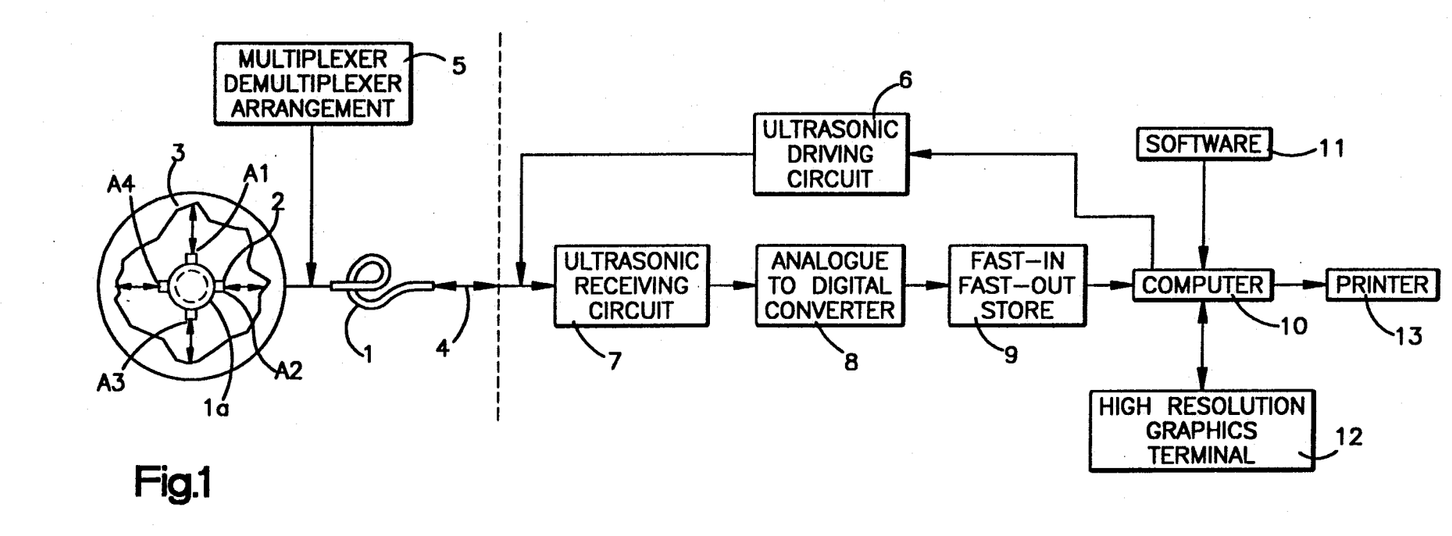
FIG. 1 is a block diagram of a system according to one aspect of the present invention.

FIG. 1

FIG. 1 is a block diagrammatic representation of a method and apparatus for providing an image of the interior of a human organ particularly an artery and is the same as FIG. 1 in our U.S. Pat. No. 5,081,993.

A catheter 1 for insertion into a human artery 3 has a distal end 1a on which is mounted an annular ultrasonic transducer assembly 2, the proximal end of the catheter being electrically connected by connection 4 to the equipment shown to the right of the broken line in FIG. 1.

The electrical connection 4 includes a wiring arrangement which acts as a multiplexer/demultiplexer 5 which functions to reduce the number of wires which would otherwise need to pass through catheter 1 in order to connect the transducer assembly 2 to the equipment illustrated diagrammatically to the right of the broken line in FIG. 1. The multiplexing/demultiplexing arrangement is shown in more detail in FIGS. 3 and 4 of our U.S. Pat. No. 5,081,993.

Other multiplexing arrangements could be used. For example an integrated circuit multiplexer could be employed particularly when a large number of crystals are being used. One or more such integrated circuit multiplexers could be used depending upon the number of crystals. One such suitable integrated circuit multiplexer is that manufactured by Precision Monolithics Model PMI-MUX-08.

The transducer assembly 2 is energised by a driving circuit 6 to cause the transducer assembly 2 to emit ultrasonic signals. The transducer assembly 2 responds to echoes of the emitted signals and this causes the generation of echo signals which pass back to the multiplexer/demultiplexer arrangement 5 to an ultrasonic receiving circuit 7 and then to an analogue-to-digital converter 8 which translates the analogue electrical echo signals into digital signals.

These digital echo signals are then fed to a fast-in-fast-out data store 9 from whence they are fed into a digital computer 10.

The digital computer 10 is programmed by means of software 11 in such a way that the digital echo signals are transformed into signals which when fed to a high resolution graphics display terminal 12 will enable a two-dimensional real-time representation of the interior of the artery 3 to be displayed.

A hard copy of the two-dimensional representation can be obtained by means of a printer 13.

The multiplexer/demultiplexer arrangement 5, the ultrasonic driving circuit 6, receiving circuit 7, the analogue to digital converter 8, the fast-in-fast-out store 9 and the digital computer 10 could be as described in our abovementioned U.S. patent.

Figure 2:
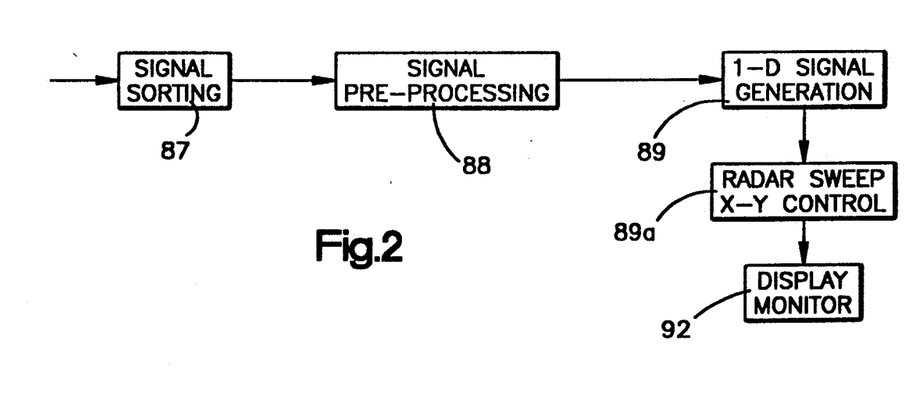
FIG. 2 is a block diagram showing in more detail parts of the system of FIG. 1.

FIG. 2

This figure is equivalent to FIG. 8 in our abovementioned U.S. patent but considerably simplified because in this aspect of the present application we are concerned with the production of a two-dimensional real-time image and not a three-dimensional non-real-time image as is the case with that earlier patent.

There are a number of ways in which the echo signals from the probe can be handled in order to produce a two-dimensional real-time representation. For example it would be possible to take signals from the "2D Image Generation Unit 93" in FIG. 18 of our aforementioned U.S. patent and feed these to an image display in real-time.

However, the preferred method is illustrated in FIG. 2 of the present application in which the same reference numerals have been used as in FIG. 18 of our aforementioned U.S. patent to represent the same units.

In this preferred arrangement the signals from the unit 89 are sorted/reordered in the unit 89A and then fed to the display device 92 either directly or, as in FIG. 18, through the Unit 94 in that Figure to improve the image quality.

Figure 3:
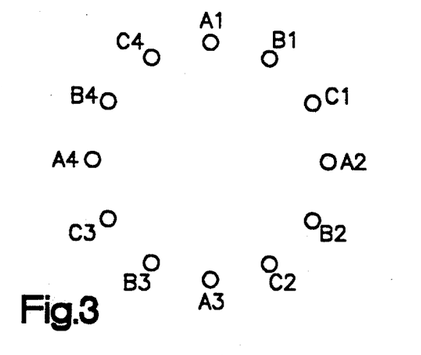
FIG. 3 illustrates the timing of the signals emanating from the unit 89 in FIG. 2.
Figure 5:
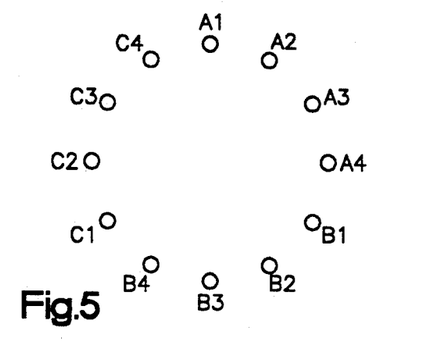

FIGS. 3 AND 5

Figure 4:
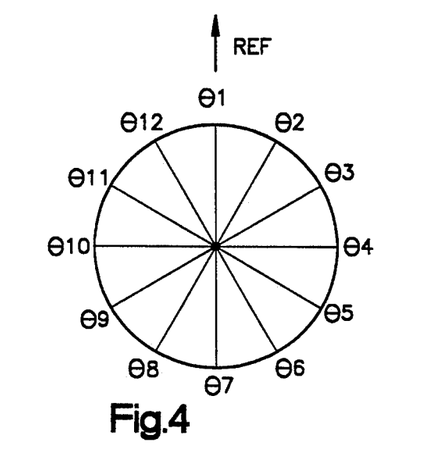
FIG. 4 and 5 illustrate two ways in which the signals from the unit 89 can be recorded for display purposes.

The meaning of the term "sorting/reordering" will now be explained with reference to FIGS. 3 to 5 of the present application.

In the system disclosed in our abovementioned U.S. patent the probe has twelve transducer elements which are fired in three groups of four, namely a group consisting of element A1, A2, A3, A4 and B1, B2, B3, B4 and C1, C2, C3, C4. This is illustrated in FIG. 3A in that earlier patent application and essentially the same arrangement is shown in FIG. 3 of the present application except that the points on the present drawings do not represent the transducers themselves.

With the system of the earlier copending international patent application the group of transducer elements A1, A2, A3 and A4 are fired simultaneously followed by the elements B1, B2, B3 and B4 followed by the elements C1, C2, C3 and C4 which in turn are followed by A1, A2, A3, A4 and so on. By having this pattern of firing the transducers the echo signals from each group of four transducers enables the position of the axis of the probe/catheter to be identified in relation to the axis of the artery. This would not be the case if, for example, the transducers were fired in the groups A1, B1, C1, A2 followed by B2, C2, A3, B3 and then by C3, A4, B4, C4 and so on.

The echo signals resulting from the firing of the transducers in the pattern illustrated in FIG. 3 and described immediately above are however, stored in the computer contiguously i.e. after A1 there is A2 and then A3 and then A4 so that if signals were taken straight out from the computer to the display in that order they would be in the wrong order to produce the correct image. It is therefore necessary to recorder these signals for display purposes.

This requirement can be satisifed in two ways. The first requires that the stored signals be read-out contiguously as they are stored but with the sweep angle $\theta$ of the display system (FIG. 4) being modified so as to place the signal data along the appropriate radii on the display. Thus the sweep angle would be modulated in the order $\theta 1, \theta 4, \theta 7, \theta 10, \theta 2, \theta 5, \theta 8, \theta 11, \theta 3, \theta 6, \theta 9, \theta 12$. Thus modulation of $\theta$ can be readily achieved by an active electronic circuit controlling the X-Y electron guns of the display tube.

An ideal implementation would incorporate a RAM element which contained the sweep angles in order and the contents of which could be readily modified from software. Thus a change in the scanning sequence or an increase in the number of transducer elements could be readily accommodated.

The second approach preserves a linear increment in the sweep angle (i.e. $\theta 1, \theta 2, \theta 3, \theta 4, \theta 5, \theta 6, \theta 7, \theta 8, \theta 9, \theta 10, \theta 11, \theta 12$) but requires a consequent reordering of the data in memory to achieve a correct display. The recording algorithm is straightforward and its function is illustrated in FIG. 5. This task could be achieved either in hardware or software, the latter being preferred on the grounds of flexibility of system control.

The latter of these two schemes, i.e. FIG. 5 is to be preferred in terms of simplicity of implementation. However, for both schemes, the software overhead is low and therefore is readily executable in real-time. If the software overhead were to become too onerous, for example due to a large increase in the number of transducer elements, then special digital hardware circuits could be introduced to perform the tasks rapidly but which retain the advantages of programmability.

Figure 6:
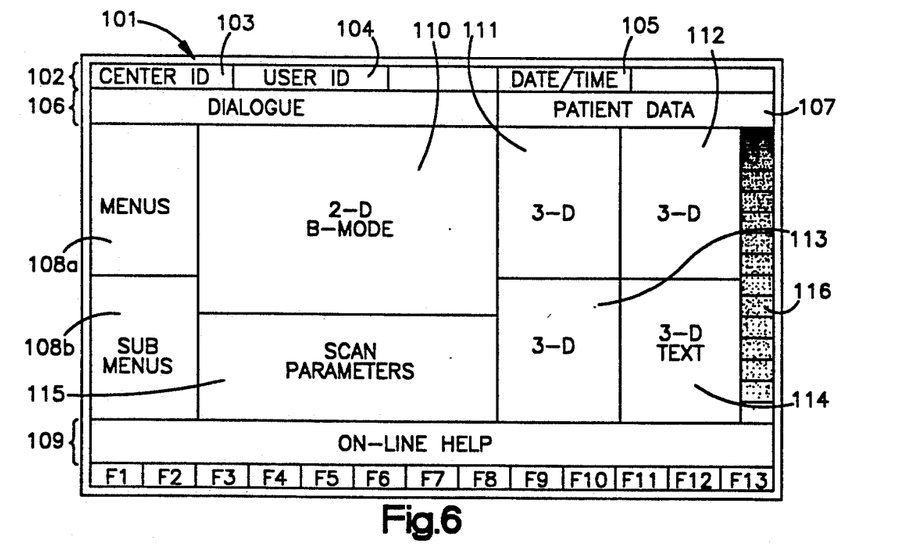
FIG. 6 is a diagrammatic representation of a work station display screen embodying another aspect of the present invention.

FIG. 6

The system just described for presenting the clinical team with a two-dimensional real-time image can be combined with the system disclosed in our U.S. patent to enable the clinical team to have both the real-time two-dimensional image and also the ability to see a three-dimensional representation of the organ (e.g. artery) being examined and/or operated on.

The kind of display which the present invention can provide is shown diagrammatically in FIG. 6 and will now be described.

It is known at the present time that electronic work stations are available which employ architectures with bit-mapped display units and a software "windowing" environment by which more than one display can be shown on a single CRT display screen. An appropriate known workstation for such a windowing software architecture is that known as the "X-windows system". This is virtually an industry standard graphical user interface (GUI) and has been largely developed by the Massachusets Institute of Technology (MIT). It provides a network-transparent and vendor-independent operating environment and supports concurrency, that is several applications/tasks can be active at any one time.

The current version of "X-windows" from MIT is known as the X11. The X11 can be ported onto proprietary hardware platforms. For example the Digital Equipment Company (DEC) have released what are known as "DEC windows". For further information concerning these so called "X-windows" reference is made to the article by Oliver Jones entitled "Introduction to the X-Window System" published by Prentice Hall 1989.

This has a so-called client-server structure which faciliates efficient multi-tasking and multiprocessor operation.

With this kind of workstation, and applying the system of the present invention, it is possible to independently display the two-dimensional image in real-time and allow other display operations to take place simultaneously including the display and manipulation of a three-dimensional image in non-real time in accordance with the system disclosed in our aforementioned U.S. Patent.

This arrangement has numerous key advantages in practical terms as far as the clinical team are concerned. For example the clinician can independently use the real-time two-dimensional display to position the catheter within the desired anatomy whilst another member of the clinical team is entering scan parameters or patient data or is perhaps reviewing images taken from the patient's previous scans. Furthermore, different two-dimensional real-time images can be displayed simultaneously. For example a so-called B-mode image can be displayed together with a so-called Doppler image. Furthermore two B-mode images at different frequencies could be displayed simultaneously.

FIG. 6 illustrates diagrammatically how such a display may look on a work station CRT display screen.

At the top of the screen 101 is a zone 102 which can be set out to contain identification information such as the identification of the medical centre 103, the user identification 104, and the date and time 105. Below the zone 102 is a zone 106 which can contain patient data 107.

Down the left hand side of the screen is a zone which has a first portion 108A for menus and a second portion 108B for sub-menus. Across the bottom of the screen 101 is a zone 109 adapted to display so-called on-line help messages. Below the zone 109 are a number of so-called soft-keys labelled F1 to F13 respectively. "Soft-keys" refer to function keys with context-sensitive functionality. In other words the action of a particular function key is not uniquely defined but depends upon context in which it is being used.

The main part of the screen 101 is devoted to displaying the two-dimensional real-time image(s) together with the three-dimensional non-real-time image(s).

Specifically a two-dimensional real time B-mode image is displayed in zone 110 and three different three-dimensional non-real-time images are displayed in zones 111, 112 and 113 together with text in zone 114 which is relevant to the three dimensional images.

There is a further zone 115 which is adapted to contain scan parameters. The term "scan parameters" is used to specify to the system the values of certain scanning variables such as scan frequency, vessel size, time-gain compensation (TGC) and gain.

On the right hand side of the screen 102 is a vertical strip zone 116 which contains a grey scale and a spectrum of the colours which are available in the display.

FIG. 6 illustrates only one possible configuration of a multi-window display. Numerous other permutations may be employed the essence being that at least one two-dimensional real-time image and at least one three-dimensional non-real-time image are displayable on the screen at the same time.

The relationship between the two-dimensional and three-dimensional images will now be described with reference to FIG. 7.

Figure 7:
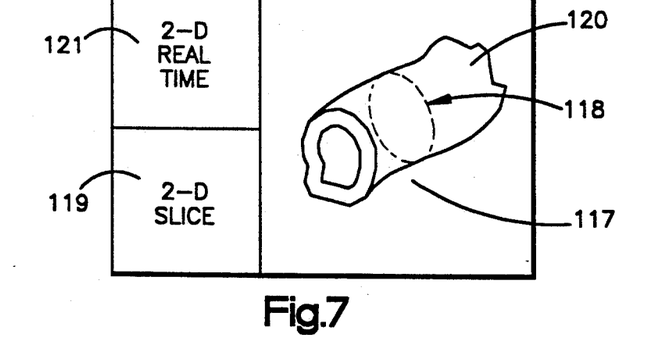
FIG. 7 is a diagrammatic representation of part of a screen display relevant to a further aspect of the present invention.

FIG. 7

As disclosed in the system of our aforementioned U.S. Patent the three-dimensional images are generated from a discrete number of two-dimensional images using a so-called "park-and-acquire" procedure as the catheter is moved through the appropriate organ e.g. an artery.

However, software can be provided within the system in order to relate the two-dimensional and the three-dimensional images in a number of different ways which would be useful to the clinician.

For example, if it is assumed that the position of the catheter within the artery is accurately known, the two-dimensional image can be related to the slice through a three-dimensional image previously acquired (displayed), that previously acquired three-dimensional image being, for example the image of the artery before treatment.

By using the arrangement generally disclosed in relation to FIG. 6, i.e. the combination of at least one two-dimensional real-time image of at least one three-dimensional non-real-time image, it would be possible to obtain the display shown in FIG. 7.

In this display the non-real-time three-dimensional image 120 is shown in the zone 117, it being indicated on that image by the arrow 118 the actual real-time two-dimensional slice 121 of an artery 120. The image 119 represents the previously acquired two-dimensional slice through the artery before treatment for comparison with the image 121. As indicated earlier, to achieve this, it is essential that the precise position of the catheter is known. This could be achieved by means of DSA matching.

The way in which the multi window displays shown in FIGS. 6 and 7 may be achieved will now be described with reference to FIGS. 8 and 9.

Figure 8:
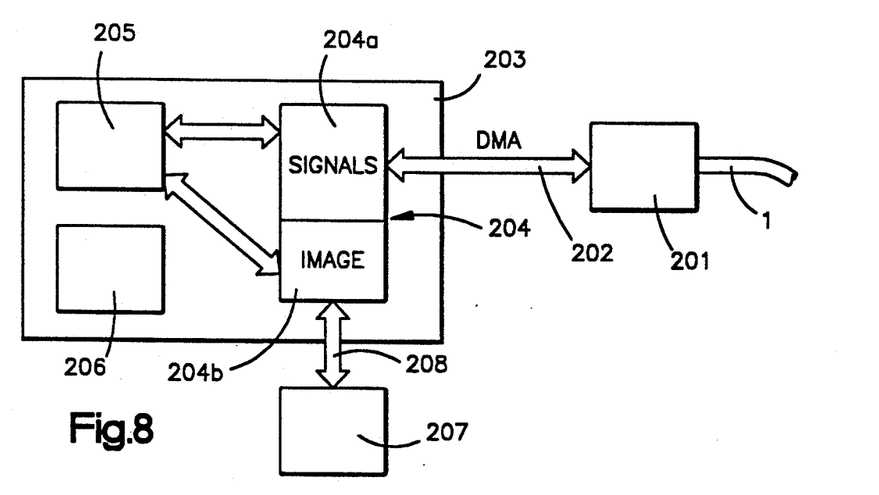
FIG. 8 is a block diagram of a parallel processing system according to a further aspect of the present invention.
Figure 9:
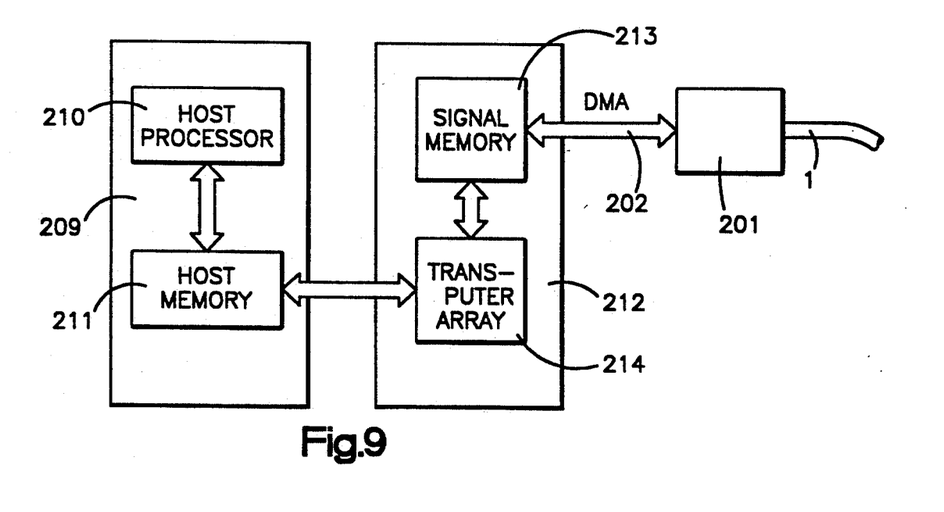
FIG. 9 is a block diagram similar to FIG. 8 of an alternative parallel processing system according to the present invention.

FIGS. 8 AND 9

The two-dimensional real-time B-mode image must be captured, processed and displayed in what will be perceived by the user as "real-time" if it is to be of any real clinical value to the user. In other words it must be able to give the clinician a feedback picture of the vascular anatomy and pathology as the clinician manipulates the catheter within the organ, such as an artery. In order to achieve this a high speed electronic processor unit would normally be required.

If in addition to this requirement for a "real-time" display one further imposes on the system the need to operate in a so-called multi-tasking mode, e.g. the simultaneous handling of the two-dimensional real-time B-mode image and the various system functions including for example the provision of a three-dimensional non-real-time image, this imposes a futher burden on the requirements for the speed of operation of the electronic processor. Although at the present time electronic processors do exist which could cope with these requirements they are relatively expensive and therefore do not necessarily provide a cost-effective solution to this problem.

The present invention therefore envisages the employment of at least two independent electronic processors which are operated in parallel in order to simultaneously execute at least two required tasks.

With such parallel processing coordination and control of the processors is of critical importance.

The present invention envisages a number of ways in which such coordination and control may be effected, two examples being shown in FIG. 8 and 9.

In the arrangement of FIG. 8 the analogue signals from the catheter 1 pass to a digital interface 201 and then via a DMA (Direct Memory Addressing) link 202 to a multiprocessor arrangement generally indicated by 203.

At the present time there is available state-of-the-art computers which employ multiple processors which can be programmed to operate in a parallel mode. One example is the product manufactured by the Digital Equipment Company and known as the DEC 3500 series workstations which employ multiple VAX processors.

The multiple processor arrangement 203 consists of a first processor 205 and a second processor 206. The processor 205 is adapted to process signals concerned with the two-dimensional real-time display. The processor 206 is adapted to process signals concerned with other functions such as the provision of a three-dimensional non-real-time image and provide overall system control.

There is a memory 204 having a part 204a concerned with the incoming signal and a part 204b concerned with storing images. A display window 207 is memory mapped via 208 to the image store 204b.

The processors 205 and 206 can operate in turn on the signals at 204a and the images at 204b.

More particularly the system software can be so constructed as to allow one of the processors to be dedicated to the control of the two-dimensional B-mode imaging process while the other processor handles other system functions plus the overall system control. To further enhance the speed of the two-dimensional imaging the signals from each of the catheter transducer elements could be directly transferred into a defined memory area within the DEC 3500 under DMA control. This memory area could be directly mapped to the designated processor and the resultant image deposited in a memory area which is directly bit mapped to the appropriate display window.

An alternative arrangement is shown in FIG. 9 in which a transputer or a transputer array could be utilised to control the acquisition of the ultrasonic signals, subsequently process the signals, reconstruct the image and transfer the image data under DMA control directly into the memory of the host processor.

In FIG. 9 the host computer is indicated at 209 and includes a host processor 210 and a host memory 211.

The transputer board is indicated by 212 and includes a signal memory 213 and a transputer array 214. Examples of transputers are those manufactured by Inmos and known as the T212 and T414. The board itself could also be a proprietary item such as that manufactured by Paracom and known as the BBK-DR11 or the Parsytec VTF.

As in FIG. 8 the catheter 1 is connected to a digital interface 201 through the DMA control link 202.

The transputer has an ideal architecture for this type of application and provides an effective and relatively low cost solution.

Other signal processing operations (see later) for example for beamforming, image enhancement or tissue characterisation could be added on-line using the same approaches or extensions to them.

The examples illustrated in FIGS. 8 and 9 have the advantage over the use of the known available sophisticated digital signal processing (DSP) chips which are available in that they allow for easy programmability of the processing functions.

Figure 10A:
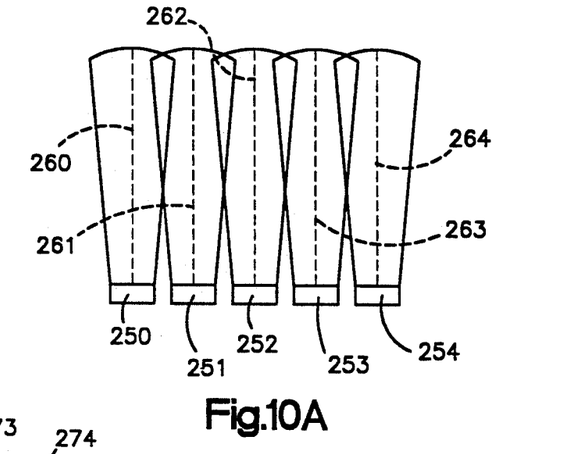
FIGS. 10A, 10B and 10C are diagrammatic representations of beam forming/steering transducer arrangements according to yet another aspect of the present invention.
Figure 10B:
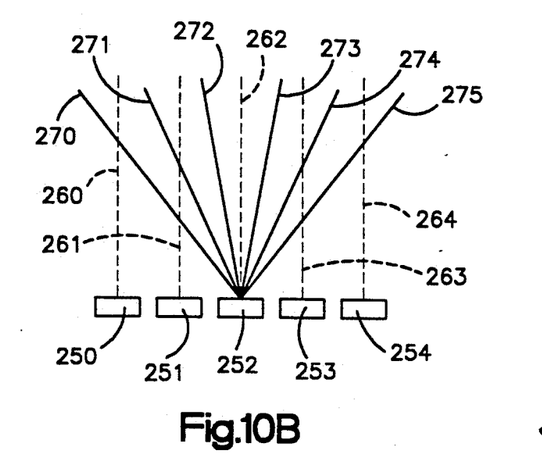
Figure 10C:
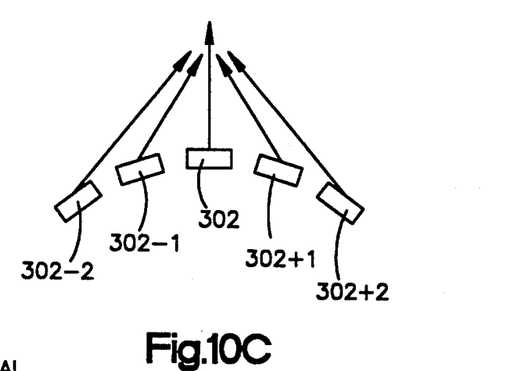

FIG. 10

There has already been described in connection with FIGS. 1 to 5, and also in our earlier U.S. Pat. No. 5,081,993, particular transducer arrangements mounted on the distal end of a catheter. In the arrangements described there are a plurality (typically twelve but it could be a greater number such as thirty-two or sixty-four) of transducer elements arranged in an annular configuration around the distal end of the catheter.

In the aforementioned described arrangements having twelve transducer elements four elements which are displaced at 90 degree intervals from one another are energised at a time, the three sets of four thus arranged elements being energised in turn to provide, as it were, a rotating cruciform beam arrangement.

In these earlier described arrangements each transducer is adapted to both transmit and also receive a resultant ultrasonic echo.

FIG. 10C illustrates an alternative arrangement the essential difference being that in this arrangement the echo signals are received on a transducer or transducers which is/are different from the transducer from which the outgoing signal originated.

More particularly, the present invention relates to employing so called beamforming and beam steering arrangements (which are known from other fields such as radar and sonar) in the kind of system described earlier in connection with FIGS. 1 to 5 and disclosed in our aforementioned U.S. Patent.

By employing beamforming and beam steering it is possible to achieve a significantly enhanced azimuthal resolution.

In order to achieve beam steering, the relative amplitude and phases of each of the transmitted or received signals must be carefully controlled to determine the beam direction and beam profile. The appropriate transducer characteristics are relatively easily calculated using models in (k, $\omega$ (omega))-space (k is the spatial frequency and $\omega$ (omega) is the temporal frequency). Examples of established beam forming methods are the so called delay-and-sum and the so-called filter-and-sum beamformers. Reference is made to the publication by Pridham R. G. and Mucci R. A. 1978 entitled "A novel approach to digital beam forming" of the Journal of the Acoustical Society of America 63 425–434 and also to the article by Dudgeon D. E. and Mersereau R. M. published in 1984 by Prentice Hall and entitled "Multidimensional digital signal processing".

FIG. 10A illustrates a conventional scanning arrangement, that is one which does not employ beamforming and beam steering. FIG. 10B in contrast illustrates a beamforming and beam steering arrangement with transducers in a straight line as in FIG. 10A. The actual arrangement employed in the present invention is shown diagrammatically in FIG. 10C in which the transducers are positioned on an arcuate path (in fact on a circular path for the whole transducer array but only part has been shown diagrammatically).

In the conventional scanning arrangement shown in FIG. 10A each transducer 250, 251, 252, 253, 254 insonates a fixed zone of space along a fixed insonation axis 260 to 264 respectively. This fixed zone of space is normally symmetrical about the central perpendicular axis of the crystal. The signal received by each transducer at each point in turn is an integral along the wave front at the equivalent distance from the transducer of the reflected ultrasound wave intensities. The resultant signal is then attributed to the axial point at the specified distance from the transducer, or alternatively can be attributed to an arc where the arc length is related to the number of crystals or the beam width. Using this approch, the anatomic surface (e.g. of an artery) is effectively being insonated only at a fixed number of points which lie on the normal axes of each transducer, thus limiting the resolution for a given number of transducers.

However if beamforming techniques are employed in order to steer the beam in a controlled way this permits the insonation to occur at points other than the fixed normal axes 260 to 264 in FIG. 10A.

A beamforming arrangement is shown diagrammatically in FIG. 10B in which the transducers have the same reference numerals and their associated normal axes have the same reference numerals as in FIG. 10A. However, with this arrangement each transducer has additional insonation axes indicated by 270, 271, 272, 273, 274 and 275, in connection with the transducer 252.

Thus, the effective azimuthal resolution of the image can be substantially increased without increasing the number of transducers. For example an effective resolution equivalent to sixty-four transducers in the arrangement of FIG. 10A could possibly be achieved in the arrangement of FIG. 10B by using only thirty two transducers.

These known beamforming and beam steering arrangements however cannot be directly employed in the system of the present invention without modification. Such modification is necessary in order to take account of the fact that the transducer elements of the present invention are mounted on a curved surface. Because of this curvature (shown in FIG. 10C) it is necessary to provide an amplitude correction for each transducer which is not firing/receiving orthogonally (that is every transducer other than the one labelled 302 in FIG. 10C). A phase correction is also required to allow for the additional propogation path which exists for the transducers which are not firing or receiving orthogonally.

In the arrangement shown in FIG. 10C there are five transducers lying on an arc of a circle the central one being labelled 302 the two on the right hand side of it being labelled 302+1 and 302+2 and the two on the left hand side of it being 302−1 and 302−2 respectively.

It is envisaged that an ultrasonic beam can be generated by such an arrangement and electronically steered to sweep the interior wall of an artery to provide a high resolution image without having to resort to arrangements proposed in the prior art such as having transducers which are rotatably mounted at the distal end of the catheter. Such arrangements have the disadvantage of moving parts which are subject to wear and obstruction and present a potential hazard to the patient.

With the beam forming and beam steering arrangement envisaged by the present invention the movement of the beam is achieved electronically thus overcoming the disadvantages outlined above.

As indicated earlier, with the arrangement illustrated in FIG. 10C it is necessary to apply an amplitude and phase correction to those transducers which are not firing/receiving orthogonally i.e. all those except transducer 302.

More particularly these corrections should be such that the amplitude correction to transducers 302−1 equals the amplitude correction to the transducer 302+1 and similarly the amplitude correction to transducer 302−2 should equal the amplitude correction to the transducer 302+2.

Similarly the phase corrections applied to 302−1 should equal that applied to 302+1 and so on.

Figure 11:
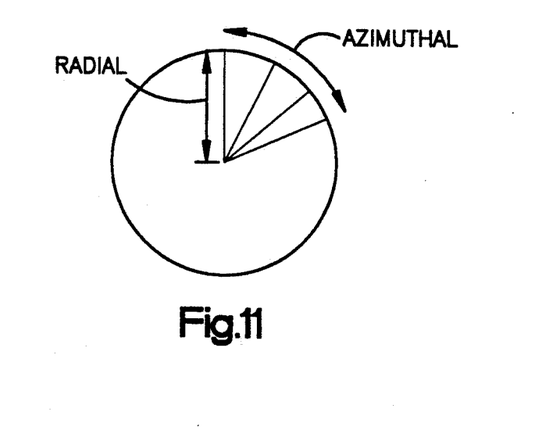
FIG. 11 is a diagrammatic representation relating to signal processing applied to the present invention.

FIG. 11

With the system of the present invention, because of the use of a digital computer and the fact that the images are generated by manipulating digital signals it is possible to achieve significant improvements in the quality of the images as compared with prior art systems which are based on the use of analogue signals.

In particular signal processing techniques can be employed to significantly enhance the quality of the two-dimensional image.

Examples of the these techniques include:

a) Spatial filtering of the signal from each transducer to remove unwanted noise components or enhance edge structures;

b) Spectral filtering of the transducer signals to optimise the extraction of frequency dispersion information;

c) In addition to filtering each of the transducer signals, which corresponds to filtering the image in a radial direction, spatial filtering of the signals in an azimuthal sense can be carried out to enhance the image by removing artefactual steps in the signal characteristics from adjacent transducers. In this context the term "artefact" refers to an unwanted/unexpected deviation in the image signal from its time/expected value caused by imperfections in the imaging systems hardware or signal processing algorithms. Signal steps in the azimuthal direction will manifest themselves by making the boundaries between the sectors corresponding to the various transducers stand out.

Sophisticated spatial filtering in the azimuthal direction can be used to reduce the perceived steps between sectors thereby improving the asthetic/perceptual qualities of the image. When combined with beamforming techniques to dynamically steer the beam, excellent image signal continuity can be expected in the azimuthal direction.

d) a) and c) could be combined by spatial filtering the entire two-dimensional image. This could be achieved, for example, in the Fourier domain but using a polar coordinate system. Spatial filtering can be achieved using two broad approaches. These are either convolution in the spatial domain or multiplicative filtering in the spatial frequency domain. The Fourier Transform (or related transforms) can be used to transform data between the two domains.

Most image processing operations are implemented using a cartesian coordinate system. Any point in the images labelled with spatial coordinates (x, y). The spatial frequency map of the image is likewise described using cartesian coordinates (u, v). In these situations the Fourier Transform is evaluated in a cartesian sense.

However, because the images of interest in the present invention have an inherent radial structure due to the image acquisition processes, it is potentially advantageous to represent them in polar coordinates (r, O) where:

$$r = (x+y)^{\frac{1}{2}}$$

$$\theta = \tan^{-1}(y/x).$$

Accurate representation of such images on a discrete matrix is more easily achieved in polar coordinates. The spatial frequency context of the image can likewise be expressed in polar coordinates (p, O). By rewriting the Fourier transform in polar form, spatial filtering of the image can be readily implemented in an efficient manner.

e) Signal processing algorithms featuring extraction, feature recognition and tissue characterisation are of enormous interest. It is envisaged that such algorithms might require to be implemented in real-time to act directly on the two-dimensional image.

We claim:

1. A system for providing an image of the interior of a human organ comprises a combination of the following features:
   (a) a catheter for insertion into the human body;
   (b) an ultrasonic transducer assembly mounted on the catheter;
   (c) means for energizing the transducer assembly to generate ultrasonic signals;
   (d) means on the catheter for receiving the resultant analog ultrasonic echo signals from the transducer assembly and including means for transmitting same and converting means located remote from the catheter and directly connected to the transmitting means for receiving the echo signals and converting them into digital signals before carrying out any processing of the echo signals;
   (e) a digital computer to which the digital signals are fed;
   (f) means for manipulating the digital signals to enable a two-dimensional real-time representation of the organ to be created; and
   (g) means connected to the computer for visually displaying the two-dimensional representation.

2. A system as claimed in claim 1 including a work station having means for simultaneously displaying both the two-dimensional real-time image and a three-dimensional non-real-time image.

3. A system as claimed in claim 1 in which the means for generating the two-dimensional real-time image includes at least two digital processing units adapted to operate in parallel.

4. A system as claimed in claim 1 having means for processing the digital signals received from the ultrasonic transducer elements in order to enhance the quality of the two or three-dimensional image.

5. A system of the kind for visualising the internal organs of the human body by means of ultrasonic signals emitted from and received by one or more transducer elements located on a catheter and including means on the catheter for receiving the resultant analog ultrasonic echo signals from the transducer element (s) and including means for transmitting same and converting means located remote from the catheter and directly connected to the transmitting means for receiving the echo signals and converting them into digital signals before carrying out any processing of the echo signals and means for manipulating the digital signals in a digital computer to enable a two-dimensional real-time present representation of the organ to be created, the transducer elements being arranged in a circuit which enables beam forming and beam steering to be achieved whereby the target may be swept by said beam to give enhanced resolution for a given number of transducers.

6. A system of the kind for visualising the internal organs of a human body by means of ultrasonic signals emitted from and received by one or more transducer elements located on a catheter and including means on the catheter for receiving the resultant analog ultrasonic echo signals from the transducer element (s) and including means.for transmitting same and converting means located remote from the catheter and directly connected to the transmitting means for receiving the echo signals and converting them into digital signals before carrying out any processing of the echo signals and means for manipulating the digital signals in a digital computer to enable a two-dimensional real-time present representation of the organ to be created, the transducer elements being arranged in a circuit, the system includes a workstation which has means to provide one or more windows in a display.

7. A system of the kind for visualising the internal organs of a human body by means of ultrasonic signals emitted from and received by one or more transducer elements located on a catheter and including means on the catheter for receiving the resultant analog ultrasonic echo signals from the transducer element (s) and including means for transmitting same and converting means located remote from the catheter and directly connected to the transmitting means for receiving the echo signals and converting them into digital signals before carrying out any processing of the echo signals and means for manipulating the digital signals in a digital computer to enable a two-dimensional real-time present representation of the organ to be created, the transducer elements being arranged in a circuit, the system includes means to represent image processing data in polar coordinates.

8. A system for providing an image of the interior of a human organ comprises a combination of the following features:
   (a) a catheter for insertion into the human body;
   (b) an ultrasonic transducer assembly mounted on the catheter;
   (c) means for energizing the transducer assembly to generate ultrasonic signals;
   (d) means on the catheter for receiving the resultant analog ultrasonic echo signals from the transducer assembly and including means for transmitting same and converting means located remote from the catheter and directly connected to the transmitting means for receiving the echo signals and converting them into digital signals before carrying out any processing of the echo signals;
   (e) a digital computer to which the digital signals are fed;

(f) means for manipulating the digital signals to enable a two-dimensional real-time representation of the organ to be created;

(g) means connected to the computer for visually displaying the two-dimensional representation; and (h) means for visually displaying a three-dimensional non-real-time image simultaneously and alongside the displaying of the two-dimensional representation.

9. A system of the kind for visualising the internal organs of the human body by means of ultrasonic signals emitted from and received by one or more transducer elements located on a catheter and including means on the catheter for receiving the resultant analog ultrasonic echo signals from the transducer element (s) and including means for transmitting same and converting means located remote from the catheter and directly connected to the transmitting means for receiving the echo signals and converting them into digital signals before carrying out any processing of the echo signals and means for manipulating the digital signals in a digital computer to enable a two-dimensional real-time present representation of the organ to be created, the transducer elements being arranged in a circuit which enables beam forming and beam steering to be achieved whereby the target may be swept by said beam to give enhanced resolution for a given number of transducers; and means for visually displaying a three-dimensional non-real-time image simultaneously and alongside the displaying of the two-dimensional representation.

10. A system of the kind for visualising the internal organs of a human body by means of ultrasonic signals emitted from and received by one or more transducer elements located on a catheter and including means on the catheter for receiving the resultant analog ultrasonic echo signals from the transducer element (s) and including means for transmitting same and converting means located remote from the catheter and directly connected to the transmitting means for receiving the echo signals and converting them into digital signals before carrying out any processing of the echo signals and means for manipulating the digital signals in a digital computer to enable a two-dimensional real-time present representation of the organ to be created, the transducer elements being arranged in a circuit, the system includes a workstation which has means to provide one or more windows in a display; and means for visually displaying a three-dimensional non-real-time image simultaneously and alongside the displaying of the two-dimensional representation.

11. A system of the kind for visualising the internal organs of a human body by means of ultrasonic signals emitted from and received by one or more transducer elements located on a catheter and including means on the catheter for receiving the resultant analog ultrasonic echo signals from the transducer element (s) and including means for transmitting same and converting means located remote from the catheter and directly connected to the transmitting means for receiving the echo signals and converting them into digital signals before carrying out any processing of the echo signals and means for manipulating the digital signals in a digital computer to enable a two-dimensional real-time present representation of the organ to be created, the transducer elements being arranged in a circuit, the system includes means to represent image processing data in polar coordinates; and means for visually displaying a three-dimensional non-real-time image simultaneously and alongside the displaying of the two-dimensional representation.

* * * * *